United States Patent
SenGupta et al.

(10) Patent No.: US 7,855,173 B2
(45) Date of Patent: *Dec. 21, 2010

(54) DETERSIVE COMPOSITIONS CONTAINING HYDROPHOBIC BENEFIT AGENTS PRE-EMULSIFIED USING SUB-MICROMETER-SIZED INSOLUBLE CATIONIC PARTICLES

(75) Inventors: Ashoke K. SenGupta, Barrington, IL (US); Ilona Lin, Wauconda, IL (US); Jason Harold St. Onge, Geneva, IL (US)

(73) Assignee: Amcol International Corporation, Hoffman Estates, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/492,653

(22) Filed: Jun. 26, 2009

(65) Prior Publication Data
US 2009/0263337 A1 Oct. 22, 2009

Related U.S. Application Data

(63) Continuation of application No. 11/331,248, filed on Jan. 12, 2006, now Pat. No. 7,569,533.

(60) Provisional application No. 60/643,430, filed on Jan. 12, 2005.

(51) Int. Cl.
C11D 3/37 (2006.01)
C11D 3/382 (2006.01)
C11D 1/86 (2006.01)

(52) U.S. Cl. ............... 510/417; 510/119; 510/130; 510/155; 510/235; 510/251; 510/326; 510/334; 510/353; 510/422; 510/437

(58) Field of Classification Search ............ 510/119, 510/130, 155, 235, 251, 326, 334, 353, 417, 510/422, 437
See application file for complete search history.

(56) References Cited

U.S. PATENT DOCUMENTS

| | | | |
|---|---|---|---|
| 2,800,457 A | 7/1957 | Green et al. |
| 3,041,288 A | 6/1962 | Anthony |
| 3,415,758 A | 12/1968 | Powell et al. |
| 3,516,941 A | 6/1970 | Matson |
| 3,723,325 A | 3/1973 | Parran |
| 3,870,542 A | 3/1975 | Ida et al. |
| 4,145,184 A | 3/1979 | Brain et al. |
| 4,152,272 A | 5/1979 | Young |
| 4,318,818 A | 3/1982 | Letton et al. |
| 4,387,090 A | 6/1983 | Bolich, Jr. |
| 4,402,856 A | 9/1983 | Schnoring et al. |
| 4,424,134 A | 1/1984 | Sissin et al. |
| 4,446,032 A | 5/1984 | Munteanu et al. |
| 4,446,042 A | 5/1984 | Leslie |
| 4,464,271 A | 8/1984 | Munteanu et al. |
| 4,515,705 A | 5/1985 | Moeddel |
| 4,534,891 A | 8/1985 | Boden et al. |
| 4,537,706 A | 8/1985 | Severson, Jr. |
| 4,537,707 A | 8/1985 | Severson, Jr. |
| 4,550,862 A | 11/1985 | Barker et al. |
| 4,561,998 A | 12/1985 | Wertz et al. |
| 4,597,898 A | 7/1986 | Vander Meer |
| 4,664,064 A | 5/1987 | Lowe |
| 4,673,568 A | 6/1987 | Grollier et al. |
| 4,690,825 A | 9/1987 | Won |
| 4,705,681 A | 11/1987 | Maes et al. |
| 4,710,374 A | 12/1987 | Grollier et al. |
| 4,714,562 A | 12/1987 | Roselle et al. |
| 4,767,547 A | 8/1988 | Straathof et al. |
| 4,842,849 A | 6/1989 | Grollier et al. |

(Continued)

FOREIGN PATENT DOCUMENTS

| | | |
|---|---|---|
| WO | WO-9811869 | 3/1998 |
| WO | WO-9811870 | 3/1998 |
| WO | WO-0174310 A2 | 10/2001 |

OTHER PUBLICATIONS

International Preliminary Report of Patentability for International Application No. PCT/US2006/001019 (Jul. 17, 2007) by The International Bureau of WIPO (7 pages).

(Continued)

*Primary Examiner*—Charles I Boyer
(74) *Attorney, Agent, or Firm*—Marshall, Gerstein & Borun LLP

(57) ABSTRACT

A cationic oil-in-water emulsion, for addition to detersive compositions, comprising hydrophilic cationic polymers, a surface-active, anionic polymer that is capable of adsorbing at an air-water interface or an oil-water interface and/or is oil-soluble, and a hydrophobic benefit agent in the oil phase made by adding the benefit agent to a hydrophobic liquid; thickening the oil phase with an organophillic smectite clay reacted at clay platelet surfaces to make the clay platelet surfaces hydrophobic while the edge surfaces of the clay remain hydrophilic, such that the organophillic smectite clay is adsorbed at an oil/water interface in the emulsion, and one of the hydrophilic, cationic polymers has a cationic nitrogen content of at least 6% by weight, that is incompatible with anionic surfactants, being insoluble in anionic-surfactant solutions containing an amount of 3% or higher of an anionic surfactant, and another hydrophilic cationic polymer has a cationic nitrogen content of at least 0.1% by weight and has a molecular weight of at least 600,000 Dalton.

26 Claims, No Drawings

U.S. PATENT DOCUMENTS

| | | | |
|---|---|---|---|
| 4,946,624 A | 8/1990 | Michael |
| 4,948,818 A | 8/1990 | Carmody et al. |
| 4,954,285 A | 9/1990 | Wierenga et al. |
| 4,962,133 A | 10/1990 | Chromecek et al. |
| 4,962,170 A | 10/1990 | Chromecek et al. |
| RE33,429 E | 11/1990 | Abrutyn |
| 4,968,451 A | 11/1990 | Scheibel et al. |
| 4,973,422 A | 11/1990 | Schmidt |
| 5,085,857 A | 2/1992 | Reid et al. |
| 5,112,688 A | 5/1992 | Michael |
| 5,126,061 A | 6/1992 | Michael |
| 5,137,646 A | 8/1992 | Schmidt et al. |
| 5,145,842 A | 9/1992 | Driedger et al. |
| 5,169,552 A | 12/1992 | Wise |
| 5,194,639 A | 3/1993 | Connor et al. |
| 5,207,998 A | 5/1993 | Robinson et al. |
| 5,275,755 A | 1/1994 | Sebag et al. |
| 5,288,417 A | 2/1994 | Bauer et al. |
| 5,288,431 A | 2/1994 | Huber et al. |
| 5,306,434 A | 4/1994 | Schueller et al. |
| 5,403,499 A | 4/1995 | Kiefer et al. |
| 5,411,671 A | 5/1995 | Bauer et al. |
| 5,458,809 A | 10/1995 | Fredj et al. |
| 5,458,810 A | 10/1995 | Fredj et al. |
| 5,460,752 A | 10/1995 | Fredj et al. |
| 5,466,802 A | 11/1995 | Panandiker et al. |
| 5,470,507 A | 11/1995 | Fredj et al. |
| 5,500,152 A | 3/1996 | Helliwell et al. |
| 5,543,074 A | 8/1996 | Hague et al. |
| 5,545,340 A | 8/1996 | Wahl et al. |
| 5,545,350 A | 8/1996 | Baker et al. |
| 5,559,261 A | 9/1996 | Sivik |
| 5,562,849 A | 10/1996 | Wahl et al. |
| 5,565,145 A | 10/1996 | Watson et al. |
| 5,574,179 A | 11/1996 | Wahl et al. |
| 5,581,005 A | 12/1996 | Perkins |
| 5,597,936 A | 1/1997 | Perkins et al. |
| 5,618,523 A | 4/1997 | Zysman et al. |
| 5,661,118 A | 8/1997 | Cauwet et al. |
| 5,674,832 A | 10/1997 | Keys |
| 5,677,407 A | 10/1997 | Sojka |
| 5,679,630 A | 10/1997 | Baeck et al. |
| 5,703,030 A | 12/1997 | Perkins et al. |
| 5,703,034 A | 12/1997 | Offshack et al. |
| 5,705,464 A | 1/1998 | Scheper et al. |
| 5,712,358 A | 1/1998 | Sojka |
| 5,726,138 A | 3/1998 | Tsaur et al. |
| 5,731,278 A | 3/1998 | Nair et al. |
| 5,756,436 A | 5/1998 | Royce et al. |
| 5,759,990 A | 6/1998 | Wahl et al. |
| 5,776,443 A | 7/1998 | Vinski et al. |
| 5,777,054 A | 7/1998 | Sojka |
| 5,830,960 A | 11/1998 | Sojka |
| 5,830,967 A | 11/1998 | Sojka |
| 5,834,577 A | 11/1998 | Sojka |
| 5,837,661 A | 11/1998 | Evans et al. |
| 5,837,790 A | 11/1998 | Sojka |
| 5,853,707 A | 12/1998 | Wells et al. |
| 5,877,145 A | 3/1999 | Wahl et al. |
| 5,902,781 A | 5/1999 | Painter |
| 5,914,101 A | 6/1999 | Tapley et al. |
| 5,914,307 A | 6/1999 | DeNome et al. |
| 5,916,862 A | 6/1999 | Morelli et al. |
| 5,923,203 A | 7/1999 | Chen et al. |
| 5,929,022 A | 7/1999 | Velazquez |
| 5,932,203 A | 8/1999 | Coffindaffer et al. |
| 5,935,561 A | 8/1999 | Inman et al. |
| 5,939,373 A | 8/1999 | Haeggberg et al. |
| 5,955,552 A | 9/1999 | Sojka |
| 5,962,386 A | 10/1999 | Scheper et al. |
| 5,968,286 A | 10/1999 | Crudele et al. |
| 5,968,881 A | 10/1999 | Haeggberg et al. |
| 5,990,059 A | 11/1999 | Finel et al. |
| 5,990,065 A | 11/1999 | Vinson et al. |
| 6,017,871 A | 1/2000 | Baeck et al. |
| 6,020,294 A | 2/2000 | Getty et al. |
| 6,024,943 A | 2/2000 | Ness et al. |
| 6,051,540 A | 4/2000 | Shefer et al. |
| 6,069,122 A | 5/2000 | Vinson et al. |
| 6,080,708 A | 6/2000 | Glenn, Jr. et al. |
| 6,107,429 A | 8/2000 | Sojka |
| 6,126,954 A | 10/2000 | Tsaur |
| 6,156,713 A | 12/2000 | Chopra et al. |
| 6,162,423 A | 12/2000 | Sebag et al. |
| 6,248,849 B1 | 6/2001 | Sojka |
| 6,261,483 B1 | 7/2001 | Frank et al. |
| 6,277,361 B1 | 8/2001 | Murray et al. |
| 6,329,057 B1 | 12/2001 | Dungworth et al. |
| 6,335,315 B1 | 1/2002 | Trinh et al. |
| 6,387,995 B1 | 5/2002 | Sojka |
| 6,436,383 B2 | 8/2002 | Murray |
| 6,541,565 B2 | 4/2003 | Hood et al. |
| 6,667,029 B2 | 12/2003 | Zhong et al. |
| 6,706,258 B1 | 3/2004 | Gallagher et al. |
| 6,740,631 B2 | 5/2004 | Shefer et al. |
| 6,790,814 B1 | 9/2004 | Marin et al. |
| 6,844,302 B1 | 1/2005 | Boden et al. |
| 7,118,057 B2 | 10/2006 | Hao et al. |
| 7,119,057 B2 | 10/2006 | Popplewell et al. |
| 7,119,060 B2 | 10/2006 | Shefer et al. |
| 7,122,512 B2 | 10/2006 | Brain et al. |
| 7,125,835 B2 | 10/2006 | Bennett et al. |
| 7,179,772 B2 * | 2/2007 | Keenan et al. ............. 510/130 |
| 7,196,049 B2 | 3/2007 | Brain et al. |
| 7,294,612 B2 | 11/2007 | Popplewell et al. |
| 2003/0012758 A1 * | 1/2003 | Jourdan et al. ............ 424/70.11 |
| 2003/0049282 A1 | 3/2003 | Aronson et al. |
| 2003/0224954 A1 | 12/2003 | Wells et al. |
| 2003/0228339 A1 | 12/2003 | El-Nokaly et al. |
| 2005/0158266 A1 | 7/2005 | Peffly et al. |
| 2005/0227907 A1 | 10/2005 | Lee |
| 2005/0244356 A1 | 11/2005 | Aronson et al. |
| 2006/0014655 A1 | 1/2006 | Smets |
| 2008/0131469 A1 * | 6/2008 | Hashimoto ................. 424/401 |
| 2008/0260674 A1 * | 10/2008 | Philippe ................. 424/70.13 |

OTHER PUBLICATIONS

International Search Report for International application No. PCT/US2006/001019 (Jun. 7, 2006) by the European Patent Office (2 pages).

International Search Report for International Application No. PCT/US2008/006138 (Oct. 31, 2008) by The Korean Intellectual Property Office (2 pages).

Poucher W.A. Perfumes Cosmetics and Soaps. Second Edition. 1959.

* cited by examiner

DETERSIVE COMPOSITIONS CONTAINING HYDROPHOBIC BENEFIT AGENTS PRE-EMULSIFIED USING SUB-MICROMETER-SIZED INSOLUBLE CATIONIC PARTICLES

CROSS-REFERENCE TO RELATED APPLICATION

This application is a continuation of application Ser. No. 11/331,248 filed Jan. 12, 2006, which claims the benefit of priority from U.S. provisional patent application No. 60/643,430, filed Jan. 12, 2005.

FIELD OF THE INVENTION

The present invention relates to detersive compositions that allow increased deposition of thickened, hydrophobic or oil-based benefit agents contained therein onto the substrate being cleaned, namely, the hair, skin, fabric, teeth, and hard surfaces. Cleansing products such as the conditioning shampoo, body wash, liquid soap, laundry detergent, tooth paste, and counter cleaning products, characterized for having relatively high loadings of detersive surfactants, are some of the product forms that these compositions represent. Silicone, fragrance, emollient, and antimicrobial agent are typical examples of the benefit agents.

The increased deposition efficiency of the benefit agent is attributed to the specific form in which the benefit agent is included in the detersive compositions, produced upon mixing or diluting certain cationic oil-in-water (O/W) emulsions of the benefit agent with detersive surfactants. In order to derive this deposition-enhancing form of the benefit agent, the cationic emulsions are produced by sequentially following (i), (ii) and (iii), in order to obtain the full advantage of the present invention:

i) unless the benefit agent is insoluble or only sparingly soluble in surfactant solutions, for example, as with most silicones, all benefit agents are diluted or dissolved in a suitable hydrophobic solvent that has a low solubility in surfactant solutions, including, but not limited to, triglycerides, the ester solvents known for having relatively low solubility in concentrated surfactant solutions;

ii) the oil-phase containing the benefit agent, or the silicone-based benefit agent, is thickened using a smectite clay-based thickener, a portion of whose surface is sufficiently hydrophobic to render the clay dispersible in the oil phase or the silicone phase, while the remaining portion of the clay surface is hydrophilic and preferably bears an anionic charge when wetted by an aqueous solution having a pH of greater than 5;

iii) with no heating applied, the thickened oil- or silicone-phase is emulsified in water using an emulsifier system comprised of colloidal cationic particles. The cationic particles can be inorganic or organic or hybrid of inorganic and organic. They can be in solid or liquid form. Unexpectedly, it has been found that one way to produce the cationic emulsifier particles that would serve the object of the present invention is by combining certain water-soluble cationic polymers with at least one water-insoluble anionic polymer, so long as some material property, composition, and processing requirements are met during the manufacturing of the particles. These polymeric particles bear a relatively high cationic surface charge which stabilizes them against particle-to-particle aggregation. Ordinarily, these particles do not form any particulate network structures, being stable against aggregation.

The resulting cationic emulsions of the benefit agents are highly stable against coalescence, the phenomenon that leads to the separation of the oil phase from the water phase in O/W emulsions. The stability is retained even when the emulsions are diluted with water, for example, in the amount of 1 part by weight of emulsion to 50 parts by weight of water.

In the aforementioned emulsions, the individual cationic emulsifier particles remain adsorbed on the emulsion droplets, in order to be able to function as an emulsifier. As a mechanistic element, this ensures that the cationic particles remain attached to the benefit agent-laden emulsion droplets dispersed across the entire volume of the detersive compositions described herein, since these compositions are produced by mixing the foregoing preformed, cationic emulsions of the benefit agents with detersive surfactants. The enhanced substrate-deposition of the benefit agents from the detersive compositions claimed herein is attributed to having the cationic emulsifier particles pre-adsorbed on the emulsion droplets containing the benefit agent.

In addition, by emulsifying the benefit agents using preformed, discrete particles as the emulsifier, which remain adsorbed at the oil-water interface as individual or segregated particles, the benefit agent is not subjected to encapsulation within any capsule-like enclosure. This allows full manifestation of the intended benefits (for example, fragrance emission and hair conditioning), once the benefit agents deposit on the substrates being cleaned by the detersive compositions described herein. We have also found now that the foregoing cationic emulsions of the hydrophobic benefit agents do not adversely affect the foaming properties of the claimed detersive compositions to any profound extent.

BACKGROUND OF THE INVENTION

By design, detersive surfactants, generally present in excess in products such as shampoos, body washes, liquid soaps, laundry detergents, and toothpastes are meant to remove dirt, oil, grease, and particulate matter from the hair, skin, fabric, and teeth. Nonetheless, it is desirable that one or more hydrophobic or oil-based functional materials, called herein "benefit agent" or "active", contained in these cleansing products, can be deposited and retained at relatively high levels on the substrates being cleaned, while not sacrificing detergency and foaming properties of these products. These actives, having benefits related to hair-care or skin-care or fabric-care or dental-care may range from silicones used as hair-conditioning agents, to emollient oils and fragrance used as skin-moisturizing and aesthetic or sensory property-boosting agents. The majority of these benefit agents tend to be expensive, and hence may be included in the detersive products only at relatively low to moderate levels. Adequate deposition and retention of the benefit agents on the hair, skin, fabric, and teeth, therefore, is critical to achieving the positive effects of these actives, when they are to be delivered through products like shampoos, liquid soaps, laundry detergents, and toothpastes.

The prior art includes numerous patents describing methods for improving the deposition of different hydrophobic or oily actives from detersive compositions. Majority of these reported inventions, for example, the ones described in U.S. Pat. Nos. 3,723,325, 5,085,857, 5,500,152, 5,543,074, 5,776,443, 5,853,707, 5,990,059, 5,935,561, 5,923,203, 6,126,954, 6,156,713, 6,277,361 B1, 6,436,383 B2, 6,706,258 B1, U.S. patent application 2005/0158266, and WO 98/11869 involve the use of certain polymeric materials, many of which are generally referred to as deposition polymers, comprised of various types of cationic polymer-based additives. Despite the large number of patents disclosing cationic polymer-aided methods for enhancing the deposition of benefit agents from surfactant-laden products, there is a need for substantially improving the deposition efficiency. The trends in consumer preference related to detersive hair-care products, like shampoos, illustrate this void. Most 2-in-1 shampoos (the conditioning shampoos) in the market utilize cationic polymers for enhancing silicone-deposition on the hair in order to provide for hair-conditioning. Yet, most consumers who seek high levels of hair-conditioning prefer conditioners, the non-detersive hair-conditioning products, to the detersive products like the 2-in-1 shampoos. A likely reason for this might be that with the 2-in-1 shampoos, a considerable amount of the hair-conditioning agent, silicone, is rinsed away during shampooing, despite the deposition polymer contained therein.

In light of the distinguishing features of the present invention over the prior art, it appears that one plausible cause for the inadequate performance of the cationic deposition polymers as used in the prior art is that these polymers and the benefit agents are added as separate ingredients in producing the final detersive compositions, i.e., the deposition polymer(s) is not adsorbed onto the benefit agent(s) as these ingredients are incorporated into the final compositions. Nonetheless, in order for the cationic polymer to function adequately as the deposition-aid, it must first attach onto the benefit agent. Given that all cleansing products contain relatively high loadings of anionic surfactants, and in contrast, relatively low levels of the benefit agent(s) and the deposition polymer, adequate binding of the deposition polymer onto the benefit agent may not be possible when these ingredients are added separately to the detersive compositions. It is speculated herein that the underlying reasons might be the following:

i) factors such as high concentration of anionic surfactants, and strong interaction (electrostatic) between an anionic surfactant and a cationic polymer are likely to favor association between the anionic surfactants and the cationic polymer over that between two weakly interacting, low-level ingredients, the cationic polymer and the hydrophobic benefit agent, especially considering that the commonly used cationic deposition polymers (for example, cationic cellulose and guar derivatives) are mostly hydrophilic polymers;

ii) since the amount of anionic surfactant likely to adsorb on the benefit agent would be much smaller than the amount of anionic surfactant remaining unadsorbed, the cationic deposition polymer is more likely to (associate) form complexes with the unadsorbed surfactant molecules rather than with the adsorbed surfactant molecules;

iii) being present at a much higher concentration than any cationic polymer-anionic surfactant complex that could possibly form, and having a diffusivity much higher than that of such a complex, the anionic surfactants might adsorb on the hydrophobic benefit agent far more easily than the polymer-surfactant complex; and iv) the hydrophobic benefit agent may simply dissolve in the surfactant-rich solution.

In fact, it is often theorized in the art that association between the cationic deposition polymer and the benefit agent is achieved only when the cleansing products get heavily diluted during the course of the rinsing process. Clearly, large portions of the added deposition polymer and the benefit agent would be rinsed off before this optimum dilution level is reached.

Albeit, the prior art reveals approaches other than the use of cationic deposition polymers, for example, as disclosed in the U.S. Pat. Nos. 5,726,138, 6,541,565 B2, and 6,667,029 B2, the commercial detersive products continue to rely on these polymers for the deposition of hydrophobic or oil-based benefit agents. This might be because the deposition polymer-free approaches are not commercially viable from the standpoint of cost, product stability, and bulk manufacturing.

The prior art also includes approaches where droplets of hydrophobic benefit agents are encapsulated within a capsule comprising a complex coacervate of a polycation and a polyanion, as disclosed in WO 98/11870. The encapsulated droplets have a particle size distribution such that at least 10% by weight of the droplets comprises relatively large particles having a diameter of at least 100 microns. As noted in WO 98/11870, the efficacy of the claimed compositions relies heavily on parameters such as the relative hardness/softness and the thickness of the complex coacervate, as well as the size of the droplets of hydrophobic benefit agents, which would be hard to control in a cost-effective manner, especially during bulk manufacturing. The above approach presents additional limitations: i) encapsulation of a hydrophobic agent within a capsule comprising a complex coacervate would limit realizing the benefits which could have been derived otherwise from bare (non-encapsulated) hydrophobic benefit agents (for example, fragrance emission, and hair conditioning requiring direct deposition of silicone on the hair shaft); and ii) on account of having relatively large sized droplets of the hydrophobic benefit agents in the aforementioned compositions, attaining good product stability might be difficult, while attaining merely modest stability would invariably require viscous product forms, limiting severely the scope of varying the product consistency, which in turn might be undesirable from the standpoint of product aesthetics and ease of manufacturing.

It is therefore an object of the compositions and methods described herein to provide a more efficient method than the methods described in the prior art, for the deposition and retention of hydrophobic or oil-based benefit agents from detersive compositions. It is a further object that the compositions and methods are relatively inexpensive, involves manufacturing steps that are easy to implement or control, and do not adversely affect the stability, detergency, and foaming properties of the cleansing products. A related object is to provide stable, low-cost, detersive compositions that allow significantly high deposition and retention of hydrophobic benefit agents onto substrates including the hair, skin, and fabric.

Furthermore, it would be highly convenient to have the hydrophobic benefit agents available in a form which can be incorporated easily into a final product composition. In that vein, it would be of much benefit, if such an additive-form for the benefit agent also served towards attaining an enhanced deposition of the benefit agent. Nonetheless, a critical issue to be addressed in producing this additive-form is its long-term storage stability. It is therefore a further object of the compositions and methods to provide a highly stable additive-form for the hydrophobic benefit agents, which, when incorporated into detersive compositions, leads to an increased deposition of the benefit agents.

Several of the patents cited above, for example, U.S. Pat. No. 6,706,258 B1, describe the use of preformed oil-in-water (O/W) emulsions of hydrophobic benefit agents, wherein the oil-phase containing the benefit agent, is emulsified using (anionic, nonionic) surfactant-based emulsifiers. However, in the reported inventions, wherein a cationic polymer-based additive was used in conjunction with a preformed emulsion of a hydrophobic benefit agent (or a hydrophobic benefit agent alone), the cationic polymer-based additive and the preformed emulsion (or a hydrophobic benefit agent alone) were incorporated into the final detersive composition as separately-added ingredients, i.e., no attempt was made therein to pre-adsorb the cationic polymer-based additive onto the emulsion droplets (or the hydrophobic benefit agent) and subsequently adding the polymeric additive-modified emulsion (or the hydrophobic benefit agent) as a composite ingredient in producing the final detersive composition. In fact, there is no known prior art document wherein a cationic polymer-based additive was used as part of the emulsifier system used to produce an O/W emulsion of a hydrophobic benefit agent, that is subsequently incorporated into a detersive composition, with the detersive composition exhibiting enhanced deposition of the hydrophobic benefit agent onto an intended site during use, along with good stability, and minimal detrimental effect on detergency and foaming properties, as in accordance with the compositions and methods described herein.

SUMMARY OF THE INVENTION

Described herein are compositions for use as cleansing products like shampoo, body wash, liquid soap, and laundry detergent, which allow substantive retention on the hair, skin, and fabric, of one or more hydrophobic benefit agents contained therein. According to the compositions and methods described herein, the hydrophobic actives are incorporated into the detersive compositions, by mixing or diluting certain cationic oil-in-water (O/W) emulsions of the benefit agent(s) with detersive surfactants present either in aqueous solutions or in powder/granular forms.

Although low molecular weight (molecular weight <5,000 Dalton) cationic surfactants could be used as an emulsifier, as revealed in the U.S. Pat. No. 5,306,434 involving non-detersive hair conditioner compositions, to produce the cationic surface charge of emulsion droplets, these surfactants are not preferred for the purpose of the compositions and methods described herein. With these low molecular weight emulsifiers, the emulsion stability would be only modest, while the emulsifier dosage requirement would be relatively high. More importantly, these low molecular weight compounds may not be capable of aiding the deposition of benefit agents from detersive compositions.

Emulsions stabilized by particulate- and/or polymer-based emulsifiers generally tend to exhibit a relatively high stability against flocculation and coalescence. Considering this inherent advantage with the aforementioned emulsifiers, the present invention embodies the use of these emulsifiers in producing cationic oil-in-water (O/W) emulsions of the hydrophobic benefit agents. Unexpectedly, we have found now that these cationic emulsions greatly enhance the deposition of hydrophobic benefit agents from detersive compositions onto an intended site during use, e.g., hair shaft, skin, fabric.

According to an important embodiment of the compositions and methods described herein, the emulsifier for the cationic emulsions of hydrophobic benefit agents is preferably a cationic particulate material, comprising an inorganic moiety, or an organic moiety, or a hybrid of inorganic and organic moieties. Yet another important embodiment requires that, preferably, medium to very high molecular weight cationic polymers, more preferably, high molecular weight cationic polymers having a molecular weight in the range of 300,000-1,000,000 Dalton, and most preferably, certain combinations of high molecular weight and very high molecular weight (molecular weight >1,000,000 Dalton) cationic polymers are used as an emulsifier component to render the emulsion droplets cationic. Nonetheless, in order for a cationic particulate material, or a cationic polymer to serve as an emulsifier, it is required to adsorb at the oil-water interface.

One way to achieve good interfacial adsorption of cationic polymers is to use cationic, amphiphilic copolymers that have both hydrophilic and hydrophobic segments in the polymer chain. Such copolymers could adsorb at the oil-water interface with their hydrophobic segments anchored onto the oil phase. Albeit, such copolymers might be functionally suitable for the present invention, they tend to be costly. The other type of cationic polymer that might be effective, are the hydrophobically-modified cationic polymers which also tend to be expensive.

Hydrophilic cationic polymers are relatively low-cost materials, and hence are preferred for the compositions and methods described herein. These polymers, however, may not be sufficiently surface-active for adsorption at the oil-water interface. Therefore, according to an important embodiment of the present invention, anionic polymers that are capable of adsorbing at the oil-surface are used to facilitate the interfacial adsorption of the hydrophilic cationic polymers. These anionic polymers electrostatically attract, onto themselves, the cationic polymers, serving as a coupling agent for the cationic polymers to co-adsorb at the interface. In effect, the emulsifier system is a combination of the hydrophilic cationic polymers and the surface-active anionic polymers. Another embodiment of the compositions and methods described is to have the ratio of weights of the anionic and cationic components of the emulsifier system such that the emulsion droplets are cationic. Yet another embodiment is to use water-insoluble, hydrophobic, anionic polymers as the anionic component of the emulsifier system.

As indicated above, the most preferred option for the cationic component of the emulsifier system is to use certain combinations of high molecular weight (molecular weight in the range of 50,000-600,000 Dalton) and very high molecular weight (molecular weight >600,000 Dalton) cationic polymers. Since a very high molecular weight polymer can flocculate emulsion droplets by what is known as bridging flocculation, in the context of the present invention, in accordance with the high molecular weight cationic component embodiment, it is important that the cationic charge of the emulsion droplets is relatively high, for example, wherein the droplets show a cationic zeta potential of more than 25 millivolts, as measured using the methods known in the art. Bridging flocculation of suspended particles occurs when a single polymer chain simultaneously adsorbs on more than one particle. Accordingly, before undergoing bridging flocculation by a polymer chain, two or more suspended particles must approach one another as closely as where the particle-to-particle separation distance is equal to or less than the length of the polymer chain. Such close approach of the suspended particles may not be possible if there is sufficient electrostatic repulsion between the particles due to their surface charge, inhibiting the prospects of bridging flocculation even by a very high molecular weight polymer.

It was found during the research leading to the compositions and methods described herein that concentrated emulsions of hydrophobic benefit agents could be produced more easily, using the aforementioned emulsifier system, if the oil- or silicone-phase was thickened using a specific type of a particulate-based thickener, prior to emulsification. The most widely used particulate-based thickeners include the layered silicate materials such as the smectite clays, namely the bentonite and hectorite clays, as well as fumed metal oxides, for example, silica. Layered silicate materials are a class of inorganic particulate materials that occur as stacks of individual, planar silicate layers referred to as platelets in the clay literature. These materials, as well as fumed silica, however, are hydrophilic in terms of surface property. Therefore, unless their surface is rendered hydrophobic, these materials can be used only as thickeners for water-based compositions but not for hydrophobic liquids. Various methods are known in the art for hydrophobic surface-modification of these materials, including treating the materials with long-chain (C12-C22) quaternary ammonium compounds, amphiphilic copolymers, and silanes.

In order to achieve the full advantage of the compositions and methods described herein, the specific type of particulate-based thickeners that are suitable include the hydrophobically-modified smectite clays for which only the face-surfaces of the clay platelets are rendered hydrophobic by the adsorption of long-chain (C12-C22) quaternary ammonium compounds, while the edge-surfaces remain hydrophilic. Among the particulate-based thickeners, the materials that lend themselves easily to selective surface-modification are the smectite clays, because of the differences in the surface properties of the face and edge surfaces of the clay platelets. The face-surfaces of smectite clays bear an anionic charge due to the isomorphic substitution of aluminum by magnesium in the clay-crystal structure. On the other hand, the electrical charge of the edge-surface depends on the type (anionic or cationic) of potential determining ions that adsorb on the surface when the clay platelets are dispersed in water or in an electrolyte solution. Under controlled solution (water-based) conditions, long-chain (C12-C22) quaternary surfactants can be made to adsorb only on the face-surfaces of clay platelets via ion-exchange, acting as counterions for the anionic platelet surface charge. The typical loading level for the quarternary ammonium compound can be in the range of about 30-80% by weight of dry smectite clay.

Yet another embodiment of the compositions and methods described herein pertains to the hydrophobic or oil-based benefit agents (e.g., fragrances) that are appreciably soluble in concentrated solutions of detersive surfactants, typically used in various cleansing products. According to the compositions and methods described herein, such benefit agents are either dissolved or diluted in one or more hydrophobic solvent that has a relatively low solubility in concentrated surfactant solutions, in order to minimize the dissolution of the benefit agent in the detersive surfactant solutions. These hydrophobic solvents have a solubility of less than 2% by weight in an aqueous surfactant solution containing at least 3% by weight of one or more surfactant. The oil-phase, comprising one or more benefit agent and the hydrophobic solvent, is subsequently thickened using an organophilic smectite clay of the type noted above, followed by emulsification of the thickened oil-phase using the aforementioned emulsifier system. The concentrated emulsions thus produced are eventually mixed or diluted with detersive surfactants to produce the cleansing compositions described herein.

DETAILED DESCRIPTION

The detersive compositions described herein comprise the following ingredients:
Detersive surfactants, which may consist of one or more surfactants selected from anionic, nonionic, amphoteric, and zwitterionic surfactants and mixtures thereof;
Benefit agent selected from hydrophobic or oil-based compounds, offering hair-care, skin-care, and/or aesthetic or sensory property-boosting benefits.

Depending on the type of cleansing products in which they are used as, i.e., shampoo, liquid soap, bodywash, laundry detergent, toothpaste, antiseptic ointments, these compositions may further contain ingredients selected from fatty alcohols having 8 to 22 carbon atoms, opacifiers or pearlescers such as ethylene glycol esters of fatty acids (e.g., ethylene glycol distearate), viscosity modifiers, buffering or pH adjusting chemicals, foam boosters, perfumes, dyes, coloring agents or pigments, herb extracts, preservatives, hydrotopes, enzymes, bleaches, fabric conditioners, optical brighteners, antioxidants, stabilizers, dispersants, soil release agents, anti-wrinkle agents, chelants, anti corrosion agents, and teeth cleansing and whitening agents, and mixtures thereof.

In producing these detersive compositions, the benefit agents are incorporated into the compositions by mixing or diluting cationic oil-in-water (O/W) emulsions of thickened hydrophobic benefit agent(s) with detersive surfactants present either in aqueous solutions or in powder/granular forms. The cationic emulsion of the benefit agent(s) is produced using an emulsifier system comprising of mixtures of certain hydrophilic cationic polymers and oil-soluble and/or surface-active anionic polymers. In effect, the benefit agent(s) is contained in these emulsions as a viscous, emulsified oil-phase, in the form of a composite of discrete, interfacially-adsorbed (i.e., adsorbed at the oil-water interface) cationic particles comprised of the foregoing polymers, and a thickened oil-phase. The benefit agents that have appreciable solubility in concentrated (amount $\geqq 3\%$ by weight) surfactant solutions, are first dissolved or diluted in a suitable hydrophobic cosmetically acceptable liquid or solvent that has a relatively low solubility in concentrated surfactant solutions. A particularly useful cosmetic-solvent is a triglyceride. Preceding emulsification, the oil-phase with the benefit agent(s) contained therein, is thickened using one or more organophilic smectite clay for which only the face-surface of the clay platelets is rendered hydrophobic, while the edge-surface remains hydrophilic.

The various aspects of the aforementioned detersive compositions are discussed in greater detail below:

Detersive Surfactants

Non-limiting examples of suitable anionic surfactants are the sodium, ammonium, and mono-, di-, and tri-ethanolamine salts of alkyl sulfates, alkyl ether sulfates, alkaryl sulfonates, alkyl succinates, alkyl sulfosuccinate, N-alkoyl sarcosinates, alkyl phosphates, alkyl ether phosphates, alkyl ether carboxylates, and α-olefin sulfonates. The alkyl groups generally contain from 8 to 18 carbon atoms and may be unsaturated. The alkyl ether sulfates, alkyl ether phosphates, and alkyl ether carboxylates may contain from 1 to 10 ethylene oxide or propylene oxide units per molecule, and preferably contain 2 to 3 ethylene oxide units per molecule. Examples of the most preferred anionic surfactants include sodium or ammonium lauryl sulfate and sodium or ammonium lauryl ether sulfate.

Suitable nonionic surfactants include, but not limited to, aliphatic, primary or secondary linear or branched chain alcohols or phenols with alkylene oxides, generally ethylene oxide and generally 6-30 ethylene oxide groups. Other suitable nonionic surfactants include mono- or di-alkyl alkanolamides, alkyl polyglucosides, and polyhydroxy fatty acid amides.

The amphoteric surfactants suitable for use in the present invention include alkyl amine oxides, alkyl betaines, alkyl amidopropyl betaines, alkyl sulfobetaines, alkyl glycinates, alkyl carboxyglycinates, alkyl amphopropionates, alkyl amidopropyl hydroxysultaines, acyl taurates, and acyl glutamates wherein the alkyl and acyl groups have from 8 to 18 carbon atoms.

The level of detersive surfactants may range from 1 to 95%, preferably from 2 to 90%, and most preferably from 3 to 90% by weight of the detersive compositions.

Benefit Agents

In the compositions and methods described herein, benefit agents are hydrophobic materials, including water-insoluble but oil-soluble/miscible/dispersible organic solids and liquids, as well as oily materials, that can provide a positive or beneficial effect to the substrate being cleaned, e.g., to the hair, skin, fabric, and teeth. Preferred benefit agents include, but not limited to, the following:

a) silicone oils, resins, and modifications thereof such as linear and cyclic polydimethylsiloxanes, amino-modified, alkyl, aryl, and alkylaryl silicone oils, which preferably have a viscosity of greater than 50,000 cst when used as a hair conditioning agent;
b) fragrance, perfumery, and essential oils and resins;
c) organic sunscreen actives, for example, octylmethoxy cinnamate;
d) antimicrobial agents, for example, 2-hydroxy-4,2,4-trichlorodiphenylether;
e) ester solvents; for example, isopropyl myristate;
f) lipids and lipid like substance, for example, cholesterol;
g) hydrocarbons such as paraffins, petrolatum, and mineral oil
h) fish and vegetable oils
i) hydrophobic plant extracts;
j) waxes; and
k) pigments including inorganic compounds with hydrophobically-modified surface and/or dispersed in an oil or a hydrophobic liquid.

One or more of the foregoing benefit agents is included in the compositions described herein in an amount varying from 0.05 to 80%, preferably from 0.1 to 40%, and most preferably from 0.5 to 20% by weight of the detersive composition. The benefit agents are incorporated into the detersive compositions by mixing or diluting concentrated emulsions of the benefit agents with detersive surfactants, wherein in the preferred embodiment, the emulsions are produced in accordance with the following sequential steps (i) through (iii):

i) unless the benefit agent is insoluble or only sparingly soluble in surfactant solutions, for example, as with most silicones, the benefit agent is dissolved or diluted in a hydrophobic liquid or solvent with poor surfactant-phase solubility (herein defined as having a solubility <2% by weight in an aqueous detersive surfactant solution with a surfactant content in the range of 3-25%). A preferred solvent is a triglyceride, castor oil. The triglyceride-content of the resulting oil-phase is preferably at least 50% by weight, e.g., 50-95% by weight, while the amount of the benefit agent is the range of 0.1-50%.
ii) The oil-phase containing the benefit agent, or the silicone-based benefit agent, is thickened using an organophilic smectite clay. Not all commercially available organophilic smectite clays are ideal for obtaining the full advantage of the compositions and methods described herein. The preferred organophilic smectite clays are those for which only the face surface is rendered hydrophobic by the adsorption of fatty quaternary ammonium compounds with 12 to 22 carbon atoms in the alkyl chain, while the edge-surface remains hydrophilic. Examples of suitable organoclays include, but not limited to, the organophilic bentonite clays available from Nanocor, a subsidiary of AMCOL International Corporation. The amount of organoclay added to the oil- or silicone-phase can be 3-60% by weight, preferably 20-50%, and ideally 25-45%, based on the weight of the oil- or silicone phase. In order to enhance the thickening ability of the organoclay, one or more polar materials such as propylene carbonate, ethanol, alkylene glycol, and water and mixtures thereof may be added at the level of 10-60% by weight, based on the weight of the organoclay. In producing the thickened oil- or silicone-phase, the organoclay is dispersed in the hydrophobic liquid using high-shear equipment such as rotor-stator homogenizer and extruder.
iii) The thickened oil- or silicone-phase is emulsified in water using an emulsifier system comprising of three polymeric components, an anionic polymer and two hydrophilic cationic polymers, as described in more detail to follow. However, not all three components of the emulsifier system are added to the emulsion batch at the same time. Two of the three components, the anionic polymer, and one of the cationic polymers are added to the batch prior to adding the third component. These two components are collectively referred to herein as part A of the emulsifier system. The third polymeric component, added at a later stage of the emulsification process, is referred to herein as part B of the emulsifier system. As the first step of the emulsification process, the water-phase of the emulsion is prepared by combining in a given sequential fashion de-ionized water, the anionic polymer of part A of the emulsifier system, and a preservative, and subsequently homogenizing the mixture in a rotor-stator homogenizer, for example. The next step is to add the cationic polymer of part A of the emulsifier system, and subsequently homogenizing the mixture under high shear. The subsequent step is to add the thickened oil- or silicone-phase to the water-phase, while the batch remains under agitation. Subsequently, the batch is homogenized using high-shear agitation provided by a dispersion blade agitator. Once the emulsion has formed and the composition looks uniform, part B of the emulsifier system is added, and the emulsion is homogenized further.

In addition to the aforementioned ingredients, the emulsion may further contain ingredients such as one or more pH adjustment chemicals, buffering chemicals, one or more water-phase thickener selected from non-ionic and cationic polymer-based thickeners, and one or more optical brightener pigments. The amount of thickened oil- or silicone-phase in the emulsion may range from 10 to 60% by weight of the final composition, but most preferably from 25 to 45%.

The concentrated emulsions of the benefit agents thus produced are mixed or diluted with one or more detersive surfactants present either in aqueous solutions or in powder/granular forms, in producing the detersive compositions of the present invention. The concentrated emulsions are incorporated into surfactant-laden compositions at levels varying from 1 to 60% by weight of the final compositions. These emulsions are required to be such that the surface charge of the emulsion droplets is strongly cationic (as may be determined by measuring the zeta-potential of the emulsion droplets using a method known in the art), prior to mixing the emulsions with the detersive surfactants. In order to achieve the relatively high cationic charge of the emulsion droplets, the ratio of the weight of the anionic component to the weight of the cationic components of the emulsifier system may vary from 1:0.5 to 1:30, more preferably from 1:1 to 1:20, and most preferably from 1:2 to 1:10. The ratio of the weight of the cationic polymer comprising part A of the emulsifier system to the weight of the cationic polymer comprising part B of the emulsifier system is in the range of 1:0.01-1:10, more preferably in the range of 1:0.05-1:5, and most preferably in the range of 1:0.1-1:1.

Emulsifier System

As noted above, in accordance with the compositions and methods described herein, the emulsifier system used in producing the concentrated, cationic emulsions of the benefit agents is comprised of three essential components: (1) an anionic polymer that is sufficiently surface-active for adsorption at the oil-water interface; (2) a medium-to-high molecular weight, hydrophilic, cationic polymer that is virtually insoluble in 3 weight % or higher anionic surfactant solutions; and (3) a high-to-very high molecular weight, hydrophilic, cationic polymer. In mixing components (1) and (2) to produce part A of the emulsifier system, the anionic polymer is dissolved or dispersed in water, prior to adding the cationic polymer (component 2). For the anionic polymers having weak-acid groups, for example, the phosphate and carboxylate groups, a base is added prior to adding component (2), in order to ensure that these anionic groups are fully or partially dissociated, producing anionic charge sites on the polymer chain. Component (3) is preferably added at a later stage of emulsification. Although components (2) and (3) are both hydrophilic, cationic polymers, they are preferably not interchangeable in terms of their order of addition, in order to achieve the full advantage of the compositions and methods described herein.

We have found now that Part A of the emulsifier system essentially comprises a colloidally-stable particulate material having a relatively high cationic surface charge (as inferred from the zeta-potential of the dispersed particles, measured using a method known in the art), and colloidal (i.e., less than 1 micrometer) particle size (as measured using a Malvern Zetasizer, Nano-ZS, particle size analyzer). By colloidal-stability is meant stability against particle aggregation or flocculation, which may be determined using methods (e.g., determining particle size as a function of time, stability under large centrifugal forces, measuring dispersion viscosity as a function of shear-rate) known in the art.

Component (1)

This is selected from water-soluble anionic polymers, such as polyphosphate, polysulfonates (e.g., polyvinyl sulfonate, lignosulfonates), polycarboxylates (e.g. sodium polyacrylate), polysulfates (e.g., polyvinyl sulfate), and silicone polymers with a pendant anionic group selected from carboxylate, sulfate, and phosphate groups. The polymer is preferably surface-active, meaning that it can adsorb at air-water or oil-water interfaces. A surface-active moiety is generally found capable of reducing the surface tension of water, when added at a modest level of 1% by weight or less.

A preferred anionic polymer is a water-insoluble but oil-soluble, liquid copolymer of castor oil phosphate and 3-isocyanatomethyl-3,5,5-trimethyl cyclohexyl isocyanate, referred to herein as castor oil phosphate/IPDI copolymer. This liquid copolymer is preferred because of its relatively low solubility (2 weight % or lower in surfactant solutions containing 3 weight % or higher amount of surfactant) in surfactant solutions, and because the liquid form is expected to yield less rigid (i.e., softer) cationic particles used as the emulsifier in accordance with the present invention.

Component (2)

This is selected from hydrophilic, cationic polymers with a relatively high cationic charge content of least 6% by weight of cationic nitrogen group, and having a preferred molecular weight in the range of 50,000-600,000 Dalton, more preferably in the range of 200,000-500,000 Dalton, and most preferably in the range of 300,000-500,000 Dalton. According to an important embodiment, the polymer should be insoluble in concentrated solutions (amount at least 3% by weight) of anionic surfactants. Insolubility is defined as soluble less than 1.0%, preferably less than 0.5% by weight, in a 3% by weight or greater aqueous anionic surfactant solution. The most suitable polymer is poly(diallyl dimethyl ammonium chloride) which will be referred to herein as Poly(DADMAC). It has a cationic nitrogen content of about 8.67% by weight. Due to their relatively high solubility in concentrated surfactant solutions, examples of hydrophilic cationic polymers which may not be best suited to serve as component (2) of the aforementioned emulsifier system include copolymers of DADMAC and acrylamide monomers, also known as polyquaternium-7, quaternized copolymers of vinylpyrrolidone and dimethylaminomethylmethacrylate, also known as polyquaternium-11, copolymer of vinylpyrrolidone and methacrylamidopropyltrimethylammonium chloride, also known as polyquaternium 28, and cationic derivatives of natural polymers such as cellulose, starch, and guar gum. Some of these polymers, however, may be suitable as component (3) of the emulsifier system.

Component (3)

This is selected from high-to-very high molecular cationic polymers having molecular weight preferably in the range of greater than 600,000 Dalton, more preferably in the range of 2,000,000-6,000,000 Dalton, and most preferably in the range of 1,000,000-4,000,000 Dalton. The cationic charge content of these polymers is preferably in the range of 0.1-4.5% by weight of cationic nitrogen group. Examples of such polymers include cationic copolymers of acrylamide, and cationic derivatives of natural polymers such as cellulose ether polymers, guar gum, and starch. The most preferred component (3)-polymer are the cationic derivatives of cellulose and guar.

The following examples will more fully illustrate the preferred embodiments within the scope of the present invention. These examples are solely for the purpose of illustration and are not to be construed as limitations of the present invention as many variations thereof are possible without departing from the purview and spirit of the compositions and methods described herein.

EXAMPLE I

This example shows the thickened compositions of some benefit agents that could be used in producing the detersive compositions of the present invention. In producing the thickened fragrance composition (shown in Table I), the fragrance material(s) was first mixed with a triglyceride, castor oil. The organoclay was added to this mixture in small portions, while the batch remained under mixing in a rotor-stator homogenizer (Silverson). Once the entire amount of the organoclay was added, the homogenizer speed was gradually increased to about 8,000-10,000 rpm, and the batch was homogenized until lump-free and viscous. The silicone- and castorlatum-based benefit agents were thickened following a procedure similar to the one above, except that these benefit agents were not diluted in a triglyceride prior to undergoing thickening. Also, once the composition appeared to be lump-free, a polar activator, propylene carbonate, was added, and the batch was subsequently homogenized further until it looked uniform and viscous. The organophilic smectite clay used in Mix Nos.

1, 3, and 5 is an organophilic sodium bentonite clay from AMCOL International Corporation, while a mixture of two different organophilic sodium bentonite clays was used in Mix No. 4.

TABLE I

| Ingredient | Mix 1 Benefit Agent: Fragrance | Mix 2 Benefit Agent: Castorlatum | Mix 3 Benefit Agent: Silicone | Mix 4 Benefit Agent: Silicone | Mix 5 Benefit Agent: Silicone |
|---|---|---|---|---|---|
| Triglyceride: Castor Oil | 48.13 | | | | |
| Fragrance | 24.07 | | | | |
| Castorlatum[1] | | 72.71 | | | |
| Dimethicone Fluid, 60,000 cst | | | 29.35 | | 11.58 |
| Dimethicone Fluid, 10,000 cst | | | 15.05 | 15.19 | |
| Dimethicone, 5,000 cst | | | 22.17 | | |
| Dimethicone, 350 cst | | | | 46.24 | 38.61 |
| Dimethicone, Gum[2] | | | | 20.48 | 19.31 |
| Phenyl Trimethicone | | | | | 7.72 |
| Bentonite Clay[3] | | 15.78 | | | |
| Organophilic Bentonite Clay[4] | 27.8 | | 25.67 | 14.38 | 18.53 |
| Fatty Quaternary Ammonium Compound[5] | | 8.61 (6.46-active) | | | |
| Propylene Carbonate | | 2.9 | 7.76 | 3.71 | 4.25 |

[1]A proprietary blend of castor oil and hydrogenated castor oil from CasChem
[2]SF 76 from General Electric Silicones
[3]Sodium Bentonite clay from AMCOL International Corporation
[4]Organo-34 from AMCOL, Bentone 34 from Elementis
[5]Q2C from Tomah products, 75% active

EXAMPLE II

This example presents the typical composition and manufacturing procedure for the cationic emulsions of benefit agents, produced in accordance with the present invention. The cationic polymer for the part A of the emulsifier system is poly(DADMAC), Zetag 7122 (20% active), received from Ciba Specialty Chemicals. The anionic polymer for the part A of the emulsifier system is castor oil phosphate/IPDI copolymer, Polyphos PPI-CO, received from Alzo International Inc. The cationic polymer for the part B of the emulsifier system is cationic hydroxyethyl cellulose, Ucare Polymer JR 30M, received from Amerchol Corporation.

In producing the part A of the emulsifier system, the anionic polymer (water-insoluble) was dispersed (resulting in a pale white-colored dispersion) in de-ionized water after adding a 50% solution of sodium hydroxide to the water, using a rotor-stator homogenizer (Silverson). Zetag 7122 was added next, slowly, while the batch was being homogenized at a speed of about 5,000-7,000 rpm. Once the addition of Zetag 7122 was complete, the batch was homogenized at a speed of 7,000-8,000 rpm, while maintaining ambient temperature (20-25° C.) for the batch by applying cooling. Typically, when the batch comprised a total weight of about 1.5-2 kg, based on the above ingredients, it was homogenized for a period of about 10 minutes. During the course of this homogenization process, the dispersion batch exhibited a milky white appearance. Subsequently, a small amount of a preservative, phenonip, received from Clariant, was added to the batch, following which the batch was homogenized for an additional 10 minutes. The resulting dispersion would typically exhibit the following characteristics in terms of particle size: i) when diluted by about 2.8× with water, the dilute dispersion would filter through a Whatman grade No. 40 filter paper under an applied suction, leaving virtually no solid residue on the filter paper; ii) the particle size distribution measured on a Malvern Zetasizer particle size analyzer would indicate that the particle size is in the colloidal range, i.e., less than 1 micrometer; and iii) the particles are sufficiently small for to be able to resist centrifugal separation (i.e., virtually no separation of the dispersed material) when the dispersion (having a Brookfield viscosity of <200 cps for the spindle-speed range of 1-10 rpm) is centrifuged at 4,500 rpm for a period of 30 minutes.

Once the part A of the emulsifier system was produced as described above, the thickened benefit agent-phase was added to the batch in small portions, while keeping the batch under high-speed agitation using a dispersion blade agitator. The mixture was homogenized adequately under high-shear agitation to form a homogeneous emulsion. Polymer JR 30M was added next in the form of an aqueous solution containing 2% by weight of the polymer. The emulsion was homogenized further, following the addition of the polymer solution. The composition for the resulting final emulsion is presented in Table II, wherein the Brookfield viscosity of the final emulsion is at least 10,000 cps at 1 rpm of spindle speed.

TABLE II

| Phase | Ingredient | Weight % (within ±0.01%) |
|---|---|---|
| Part A of the Emulsifier System | | |
| Water | Deionized water | 18.43 |
| | 50% Sodium Hydroxide | 0.12 |
| | Castrol Oil Phosphate/IPDI Copolymer | 0.69 |
| | Zetag 7122 (20 wt. % active) | 17.00 (3.4 active) |
| | Phenonip | 0.41 |
| Thickened Benefit Agent | | |
| Oil | Thickened Benefit Agent | 39.10 |
| Part B of the Emulsifier System | | |
| Water | 2% Polymer JR-30M Solution (2 wt. % active) | 24.25 (0.49 active) |

EXAMPLE III

This example describes the composition, manufacturing procedure, and performance properties of the detersive compositions produced in accordance with the preferred embodiments.

Composition

Conditioning (i.e., 2-in-1 type) shampoos, Shampoo Nos. 1 and 2, were manufactured using a dimethicone (silicone) emulsion prepared as per the specifications in EXAMPLE II, wherein the thickened silicone composition corresponds to Mix No. 5 in Table I of EXAMPLE I. The thickened silicone compositions used in producing the dimethicone emulsions contained in Shampoo No. 3 and in Bodywash No. 1, as per the specifications in EXAMPLE II, correspond to Mix Nos. 4 and 3, respectively, in Table I. Bodywash No. 2 contained a castorlatum emulsion produced as per the specifications in EXAMPLE II, using the thickened castorlatum composition of Mix No. 2 in Table I.

tories washed the panelist's hair first with a clarifying shampoo free of silicone and any other hair-conditioning agent, in order to wash off any residual hair-conditioning agent from

TABLE III

| Phase | Ingredients | Shampoo 1 | Shampoo 2 | Shampoo 3 | Bodywash 1 | Bodywash 2 |
|---|---|---|---|---|---|---|
| A | Deionized Water | 23.150 | 25.650 | 24.480 | 1.575 | 11.480 |
| A | Hydroxyethyl Cellulose[1] Solution | 10.000 (2% active) | 10.000 (2% active) | 8.92 (2.5% active) | 2.000 (1% active) | 4.400 (2.5% active) |
| B | Ammonium Laureth-3 Sulfate (28% active) | 35.725 | 35.725 | 35.725 | | 33.750 |
| B | Ammonium Lauryl Sulfate (28% active) | 21.425 | 21.425 | 21.425 | | 11.250 |
| B | Cocamidopropyl Betaine (31% active) | | | | | 17.420 |
| B | Ammonium Laureth-2 Sulfate (25.5% active) | | | | 47.100 | |
| B | Disodium Laureth Sulfosuccinate (32% active) | | | | 21.875 | |
| C | Cocamide MEA (92% active) | 1.000 | 1.000 | 1.000 | 3.000 | |
| C | Ethylene Glycol Distearate | 1.500 | 1.500 | 1.500 | 1.500 | 1.500 |
| C | Ammonium Chloride | 1.000 | 1.000 | 1.000 | | 1.000 |
| C | Sodium Chloride | | | | 1.000 | |
| D | Preservative[2] | 0.200 | 0.200 | 0.200 | 0.200 | 0.200 |
| D | Color Solution | 0.500 | 0.500 | 1.500 | 1.500 | 0.500 |
| D | Fragrance | 0.500 | 0.500 | 0.500 | 1.000 | 0.500 |
| E | Benefit Agent Emulsion | 5.000 (1.5% Dimethicone) | 2.500 (0.75% Dimethicone) | 3.750 (1.2% Dimethicone) | 19.250 (5% Dimethicone) | 18.000 (5.15% Castorlatum) |

[1]Cellosize Polymer PCG-10 from Amerchol Corporation
[2]DMDM Hydantoin (Tradename: Glydant) from Lonza Manufacturing Procedure Combine the Phase A ingredients under gentle agitation.

Add the Phase B ingredients to the batch and start heating the batch to about 75-85° C., while the batch remains under gentle agitation.

Once the temperature reaches about 60° C., add the Phase C ingredients under continued gentle agitation.

Start cooling the batch, once the solids dissolve and the batch looks uniform.

Upon cooling the batch to about 30-35° C., add the phase D ingredients.

Add phase E and continue mixing until homogeneous.

Performance Evaluation

Shampoo

A primary function or benefit of a hair-conditioning agent is to reduce the hair-combing strength, especially when the hair is wet. The silicone deposition efficiency of the shampoo compositions of the present invention was evaluated by conducting panel testing. Shampoo No. 1 of Table III was tested against a reference product comprising a leading commercial conditioner product that is rated by the manufacturer to yield a good hair-conditioning level of 5 on a scale of 1 to 10 (the higher the number, the greater the level of conditioning). The panel testing was carried out at Cantor Research Laboratories, New York, wherein a panel of ten panelists was convened at two different times, i.e., a total of twenty panelists were involved in evaluating Shampoo No. 1. The test protocol followed is as follows. A technical staff from Cantor Labora- prior use. This washing process was repeated (typically 2-3 times) until the panelist and the technician individually rated the ease of combing for the wet hair at the score of 2-3 on a scale of 1-10 (the higher the number, the greater the ease of combing). The washed hair was dried and the dried hair was tested again for ease of combing individually by the panelist and the technician, following the same scoring protocol as noted above. Subsequently, the panelist's hair was split into two halves. Shampoo No. 1 was applied on one half, and the leading conditioner on the other half of the hair. Following complete rinsing of the two treated halves of the hair with water, the panelist and the technician evaluated the ease of combing of the wet hair using the above scoring protocol. This evaluation was repeated after the hair was dried. The panelist and the technician also rated the smoothness and the shine for the two halves of the dried hair. The composite average (averaged over all panelist scores and technician scores for all panelists) rating provided by the twenty panelists and the technician is presented in Table IV, wherein the term "enhancement" denotes the difference in score for a conditioning property between post-clarifying shampoo and post-shampoo 1 or post-conditioner (i.e., Score after shampoo No. 1 treatment or the conditioner treatment−Score after clarifying shampoo treatment), wherein a positive value for the "enhancement" score signifies an improvement in the hair-conditioning property; the higher the "enhancement" value, the greater the improvement). Following the panel testing method described above, the leading conditioner was tested (involving the same twenty panelists) also against a leading commercial conditioning (2-in-1 type) shampoo that is rated by the manufacturer to yield deep conditioning. Based on certain findings, this 2-in-1 shampoo appears to resemble shampoo No. 1 considerably, in terms of levels of detersive surfactants and the conditioning agents. The leading 2-in-1 shampoo contains a cationic deposition polymer, cationic hydroxyethyl cellulose. The average ratings for the two products are also presented in Table IV (Test 2).

TABLE IV

| Enhancement of Conditioning Property | Shampoo 1 (2-in-1 type) (Test 1) | Leading Conditioner (Test 1) | Leading 2-in-1 Shampoo (Test 2) | Leading Conditioner (Test 2) |
| --- | --- | --- | --- | --- |
| Wet Combing | 3.25 | 3.15 | 1.38 | 3.5 |
| Dry Combing | 2.93 | 4.25 | 2.18 | 4.05 |
| Smoothness | 3.08 | 3.98 | 2.3 | 3.73 |
| Shine | 1.88 | 1.98 | 1.63 | 2.18 |

As evident from Table IV, the conditioning shampoo, Shampoo No. 1, an example of one embodiment of the present invention, came considerably close to matching the hair conditioning performance of a leading conditioner. In contrast, the leading commercial conditioning shampoo fell much short of the leading conditioner in providing for hair-conditioning. Based on similar panel testing as described above, it was also found that Shampoo No. 2 in Table III provided slightly better hair-conditioning, as compared to the leading commercial 2-in-1 shampoo (containing 1.2 wt. % dimethicone plus two additional conditioning oils), even though Shampoo No. 2 had a significantly lower level (0.75 wt. % dimethicone) of conditioning agent(s). Furthermore, the conditioning shampoo compositions described herein showed good foaming properties, no worse than the leading commercial conditioning shampoo. The test method used for evaluating the foaming property involves 20× dilution of the shampoo with water in a 100-mL graduated centrifuge tube, under mixing in a rotary mixer for 5 minutes, followed by noting the volume of the resulting foam in the centrifuge tube.

Bodywash

Skin moisturization, resulting from silicone deposition on the skin from Bodywash No. 1 in Table III, was evaluated by measuring the trans epidermal water loss (TEWL) before and after treatment of the skin with the bodywash, using a method known in the art. The panel testing (with six panelists) involving TEWL measurements, was carried out at Cantor Research Laboratories, New York. In order to put the results into a perspective, a leading commercial bodywash that contains cationic guar cellulose, presumably as a cationic deposition polymer, was tested alongside with Bodywash No. 1. The leading commercial bodywash product likely has a much higher (potentially as much as about 3×) level of a skin-moisturizing emollient, petrolatum, as compared to Bodywash No. 1, containing silicone as the skin-moisturizing agent. The reduction in the TEWL rate (a sign of skin moisturization) was about 2.7 unit with the leading commercial bodywash, closely followed by the 2.1 unit reduction in the TEWL rate with Bodywash No. 1.

In addition, the detersive compositions described herein have been evaluated for applications such as fabric softening (due to silicone deposition) and fragrance extension from laundry detergent wash, yielding results that further confirm the prospects of achieving good deposition of hydrophobic benefit agents from a wide variety of detersive compositions.

What is claimed is:

1. A personal cleansing and detergent composition comprising one or more detersive surfactants and one or more hydrophobic benefit agent, produced after mixing or diluting a cationic oil-in-water emulsion of the hydrophobic benefit agent with the detersive surfactants present either in aqueous solutions or in powder/granular forms, the said emulsion being produced sequentially following steps (a) and (b):
   (a) the hydrophobic benefit agent, in the form of either a hydrophobic liquid or a solution in a hydrophobic liquid, to be contained in the emulsified oil-phase of the emulsion, is thickened prior to emulsification using a hydrophobically surface modified smectite clay thickener, wherein, if prior to being thickened, the benefit agent has a solubility >2% by weight in surfactant solutions containing at least 3% by weight of detersive surfactants, then the benefit agent is first dissolved or diluted in a hydrophobic liquid or solvent having a solubility <2% by weight in surfactant solutions containing at least 3% by weight of detersive surfactants, and subsequently thickened using the smectite clay thickener;
   (b) the thickened oil-phase containing the hydrophobic benefit agent is emulsified in water using an emulsifier system comprising three polymeric components which are added individually in the following sequence to the water-phase of the emulsion, with the first two polymeric components mixed in the emulsion's water-phase under high-shear agitation, prior to adding the thickened oil-phase, and the subsequent addition of the third polymeric component:
      (i) a surface-active, anionic polymer that is capable of adsorbing at air-water interface or oil-water interface and/or is oil-soluble;
      (ii) a hydrophilic, cationic polymer with a cationic nitrogen content of at least 6% by weight, that is incompatible with anionic surfactants, being insoluble in anionic-surfactant solutions containing an amount of 3% or higher of an anionic surfactant; and
      (iii) a hydrophilic cationic polymer with a cationic nitrogen content of at least 0.1% by weight and having a molecular weight of at least 600,000 Dalton.

2. The composition of claim 1 wherein the emulsifier system, comprising a surface-active and/or an oil-soluble anionic polymer and a cationic polymer that is insoluble in 3 weight % or higher anionic surfactant solutions, produced after mixing the two polymers in the emulsion's water phase under high-shear agitation, is in the form of a particulate material, having a particle size of less than 1 micrometer, and a zeta potential of greater than +25 millivolts at a pH of 6 and higher.

3. The composition of claim 1, which when used in product forms selected from the group consisting of shampoo, body wash, detergent, antimicrobial wash, toothpaste, and hard surface cleaners, result in increased deposition and retention of hydrophobic benefit agents contained therein on the substrate being cleaned.

4. The composition of claim 1 wherein the detersive surfactants are selected from the group consisting of anionic, nonionic, amphoteric, zwitterionic surfactant, and mixtures thereof.

5. The composition of claim 4 comprising 3-95% by weight of detersive surfactants.

6. The composition of claim 1 wherein the hydrophobic benefit agent is selected from the group consisting of silicone, fragrance, emollient, antimicrobial agents, water-insoluble organic sunscreens, lipids, oils, hydrocarbons, waxes, and hydrophobically surface-modified pigments and inorganic compounds, and mixtures thereof.

7. The composition of claim 6 having 0.05% to 55% by weight of the hydrophobic benefit agent.

8. The composition of claim 1 wherein the cationic oil-in-water emulsion, with the hydrophobic benefit agent contained in the oil phase, is added for mixing with the detersive surfactants, at the level of 0.1% to 95% by weight of the compositions.

9. The composition of claim 1 wherein only the face-surface of clay platelets of the smectite clay is rendered hydrophobic by the adsorption of a fatty quaternary ammonium compound having from 12 to 22 carbon atoms, while an edge-surface of the clay platelets remains hydrophilic.

10. The composition of claim 9 wherein the smectite clay-based oil-phase thickener is 10% to 60% by weight, based on the weight of the oil-phase.

11. The composition of claim 10 wherein the thickened oil-phase is 10% to 60% by weight of the emulsion.

12. The composition of claim 1 wherein the thickened oil-phase comprises 0.1% to 36% by weight of the compositions.

13. The composition of claim 1 wherein the solvent is a triglyceride.

14. The composition of claim 13 wherein the triglyceride-based solvent is castor oil.

15. The composition of claim 14 wherein the triglyceride comprises 50% to 99% by weight of the solution of the hydrophobic benefit agent, prior to adding any oil-phase thickener to the solution.

16. The composition of claim 1 wherein the anionic polymer of the emulsifier system is selected from the group consisting of oil-soluble, anionic polymers with anionic groups selected from phosphate, carboxylate, sulfonate, and sulfate, and water-soluble anionic polymers selected from polysulfonates, polycarboxylates, polysulfates, and silicone polymers with pendant anionic groups selected from carboxylate, phosphate, and sulfate groups, that are capable of adsorbing at air-water interface or oil-water interface.

17. The composition of claim 1 wherein the component (ii) of the emulsifier system is a hydrophilic, cationic polymer having molecular weight in the range of 50,000-600,000 Dalton, and cationic charge content of at least 6% by weight of cationic nitrogen group.

18. The composition of claim 17 wherein the hydrophilic, cationic polymer is poly(diallyl dimethyl ammonium chloride).

19. The composition of claim 1 wherein the component (iii) of the emulsifier system is a hydrophilic, cationic polymer having molecular weight in the range of 600,000-10,000,000 Dalton, and cationic charge content of at least 0.1-4.5% by weight of cationic nitrogen group.

20. The composition of claim 19 wherein the hydrophilic cationic polymer is selected from cationic derivatives of each of hydroxyethyl cellulose and hydroxypropyl guar.

21. The composition of claim 1 wherein the preferred sequence of addition of the three components comprising the emulsifier system involves adding the anionic polymer first, followed by component (ii), mixing or homogenizing the two components prior to adding the thickened oil-phase, adding the thickened oil-phase and homogenizing the resulting mixture to form an emulsion, followed by adding the component (iii), and subsequently homogenizing the emulsion batch further.

22. The composition of claim 1 wherein the anionic polymer component is in the range of 0.1-5% by weight, based on the weight of the thickened oil-phase contained in the cationic emulsions of the hydrophobic benefit agents.

23. The composition of claim 1 wherein the total amount of the two cationic polymer components of the emulsifier system is from 0.5 to 30 times the weight of the anionic polymer component, with the component (iii) cationic polymer being from 0.01 to 10 times the weight of the component (ii) cationic polymer.

24. A method of manufacturing a detersive composition comprising mixing or diluting a cationic oil-in-water emulsion of a hydrophobic benefit agent with detersive surfactants present either in aqueous solutions or in powder/granular form, the said emulsion being produced sequentially following steps (a) and (b):
   (a) the hydrophobic benefit agent, in the form of either a hydrophobic liquid or a solution in a hydrophobic liquid, to be contained in the emulsified oil-phase of the emulsion, is thickened prior to emulsification using a hydrophobically surface modified smectite clay thickener, wherein, if prior to being thickened, the benefit agent have a solubility >2% by weight in surfactant solutions containing at least 3% by weight of detersive surfactants, then the benefit agent is first dissolved or diluted in a hydrophobic liquid or solvent having a solubility <2% by weight in surfactant solutions containing at least 3% by weight of detersive surfactants, and subsequently thickened using the smectite clay thickener;
   (b) the thickened oil-phase containing the hydrophobic benefit agent is emulsified in water using an emulsifier system comprising three polymeric components which are added individually in the following sequence to the water-phase of the emulsion, with the first two polymeric components mixed in the emulsion's water-phase under high-shear agitation, prior to adding the thickened oil-phase, and the subsequent addition of the third polymeric component:
      (i) a surface-active, anionic polymer that is capable of adsorbing at air-water interface or oil-water interface and/or is oil-soluble;
      (ii) a hydrophilic, cationic polymer with a cationic nitrogen content of at least 6% by weight, that is incompatible with anionic surfactants, being insoluble in anionic-surfactant solutions containing an amount of 3% or higher of an anionic surfactant; and
      (iii) a hydrophilic cationic polymer with a cationic nitrogen content of at least 0.1% by weight and having a molecular weight of at least 600,000 Dalton.

25. A method of depositing a hydrophobic benefit agent on a substrate comprising contacting the substrate with the composition of claim 1.

26. A cationic oil-in-water emulsion containing a hydrophilic cationic polymer, an oil-soluble and/or surface-active anionic polymer, and a hydrophobic benefit agent contained in an oil-phase of the emulsion, with the oil-phase thickened by a hydrophobically surface modified smectite clay thickener, the platelets of which has hydrophobic face surfaces and hydrophilic edge surfaces, the said emulsion being produced sequentially following steps (a) and (b):
   (a) the hydrophobic benefit agent, in the form of either a hydrophobic liquid or a solution in a hydrophobic liquid, to be contained in the emulsified oil-phase of the emulsion, is thickened using an organophilic smectite clay, wherein, if prior to being thickened, the benefit agent have a solubility >2% by weight in surfactant solutions containing at least 3% by weight of detersive surfactants, then the benefit agent is first dissolved or diluted in a hydrophobic liquid or solvent having a solubility <2% by weight in surfactant solutions containing at least 3% by weight of detersive surfactants, and subsequently thickened using an smectite clay thickener;

(b) the thickened oil-phase containing the hydrophobic benefit agent is emulsified in water using an emulsifier system comprising three polymeric components which are added individually in the following sequence to the water-phase of the emulsion, with the first two polymeric components mixed in the emulsion's water-phase under high-shear agitation, prior to adding the thickened oil-phase, and the subsequent addition of the third polymeric component:

(i) a surface-active, anionic polymer that is capable of adsorbing at air-water interface or oil-water interface and/or is oil-soluble;

(ii) a hydrophilic, cationic polymer with a cationic nitrogen content of at least 6% by weight, that is incompatible with anionic surfactants, being insoluble in anionic-surfactant solutions containing an amount of 3% or higher of an anionic surfactant; and iii) a hydrophilic cationic polymer with a cationic nitrogen content of at least 0.1% by weight and having a molecular weight of at least 600,000 Dalton.

\* \* \* \* \*